United States Patent [19]

Fleisch et al.

[11] Patent Number: 4,478,820

[45] Date of Patent: Oct. 23, 1984

[54] ANILINO-SUBSTITUTED ISOQUINOLINE QUINONES, PHARMACEUTICAL COMPOSITIONS AND METHOD OF USE THEREOF

[75] Inventors: Jerome H. Fleisch, Indianapolis; Winston S. Marshall, Bargersville; George J. Cullinan, Trafalgar, all of Ind.

[73] Assignee: Eli Lilly and Company, Indianapolis, Ind.

[21] Appl. No.: 429,589

[22] Filed: Sep. 30, 1982

[51] Int. Cl.$^3$ .................... A61K 9/12; A61K 31/47; C07D 217/02

[52] U.S. Cl. ................................. 424/45; 424/258; 546/139; 546/14 B

[58] Field of Search .............. 546/14 B; 424/258, 45

[56] References Cited

U.S. PATENT DOCUMENTS 3,491,101  1/1970  Allen, Jr. et al. ................ 546/146
3,857,847  12/1974  Gutzwiller et al. .............. 546/146
4,390,541  6/1983  Goldsworthy et al. .......... 424/258

OTHER PUBLICATIONS

Lora-Tamayo, M., et al., *Chem. Ber.*, 95, 2176–2181 (1962).
CA 68:12836u and *Diss. Abstr. B.*, 28(1), 114–115.
CA 77:121481f.
Fleisch et al., *J. Pharmacol. Exp. Ther.*, 209 238–243 (1979).
"Elusive Asthma-Related Molecule Synthesized", *Chemical and Engineering News*, Feb. 18, 1980, pp. 28–30.
Dahlen et al., "Allergen Challenge ... Leukotrienes $C_4$, $D_4$ and $E_4$", *Proc. Natl. Acad. Sci.*, 80, 1712–1716 (1983).
Dahlen, "Pulmonary Effects of Leukotrienes", *Acta Physiologica Scandinavica Supplementum* 512 (1983).
Turnbull et al., *Lancet*, II, 526–529 (1977).
Cromwell et al., *Lancet*, II, 164–165 (1981).

*Primary Examiner*—Glennon H. Hollrah
*Assistant Examiner*—James H. Turnipseed
*Attorney, Agent, or Firm*—Karen B. Dow; Arthur R. Whale

[57] ABSTRACT

This invention relates to a class of isoquinoline quinones, which are useful for the therapy of immediate hypersensitivity reactions, such as asthma, and in treating any condition characterized by excessive release of leukotrienes. This invention also includes a method for treating these conditions, which comprises administering to animals, including humans, an effective dose of the isoquinoline quinone compounds. A further part of this invention is pharmaceutical formulations containing these pharmacologically-active compounds.

10 Claims, No Drawings

ANILINO-SUBSTITUTED ISOQUINOLINE QUINONES, PHARMACEUTICAL COMPOSITIONS AND METHOD OF USE THEREOF

BACKGROUND OF THE INVENTION

This invention relates to a class of isoquinoline-5,8-quinones (also called 5,8-isoquinolinediones), which are useful for the therapy of immediate hypersensitivity reactions and conditions characterized by excessive release of slow-reacting substances or leukotrienes. This invention also includes a method for treating the above conditions, which comprises administering to animals, including humans, an effective dose of the isoquinoline quinone compounds.

Three references describe isoquinoline-5,8-quinones: CA 77:121481f; CA 68:12836u; and Lora-Tamayo, M. et al., "Uber Derivate des Isochinolin-chinons-(5.8)", Chem. Ber. 95, 2176-2181 (1962). Inhibition of leukotriene release is not taught by any of these references.

A copending application, Ser. No. 430,895, filed Sept. 30, 1982, describes a class of quinoline-quinones, while another copending application, Ser. No. 430,896, also filed Sept. 30, 1982, describes a class of quinoxalinediones. Both applications teach the use of the compounds to inhibit the release of leukotrienes and to treat immediate hypersensitivity reactions, such as asthma.

SUMMARY OF THE INVENTION

According to the present invention there is provided a compound of formula (I):

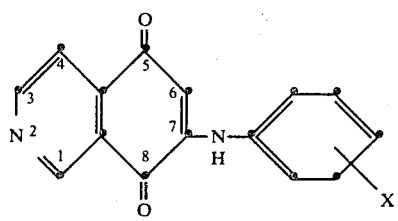

(I)

wherein
X is hydrogen, halo, or $C_1-C_3$ alkyl.

A method of treating any condition characterized by the excessive release of leukotrienes and a method of treating immediate hypersensitivity reactions such as asthma are also described. Further provided by this invention are formulations for these pharmaceutically-active compounds.

DETAILED DESCRIPTION OF THE INVENTION

In addition to the compounds of formula I, this invention also provides a method of treating an animal, including a human, suffering from or susceptible to any condition characterized by an excessive release of leukotrienes, which comprises administering to said animal a therapeutically-effective amount of a compound of formula (I) as defined above.

Also provided is a method of treating an animal, including a human, suffering from or susceptible to an immediate hypersensitivity reaction of the type represented by asthma, which comprises administering to said animal a therapeutically-effective amount of a compound of formula (I) as defined above.

According to a further aspect of the present invention there is provided a pharmaceutical formulation which comprises as the active ingredient a therapeutically-effective amount of a compound of formula (I) as defined above, associated with a pharmaceutically-acceptable carrier therefor.

The preferred compound within the scope of this invention is: 7-anilinoisoquinoline-5,8-quinone.

The following definitions refer to the various terms used throughout this disclosure. The term "$C_1-C_3$ alkyl" refers to the straight and branched saturated aliphatic radicals of one to three carbon atoms including methyl, ethyl, propyl, and isopropyl.

The term "halo" refers to chloro, bromo, fluoro, and iodo.

The preparation of the isoquinoline-5,8-quinone compounds may follow one of the reaction schemes outlined below:

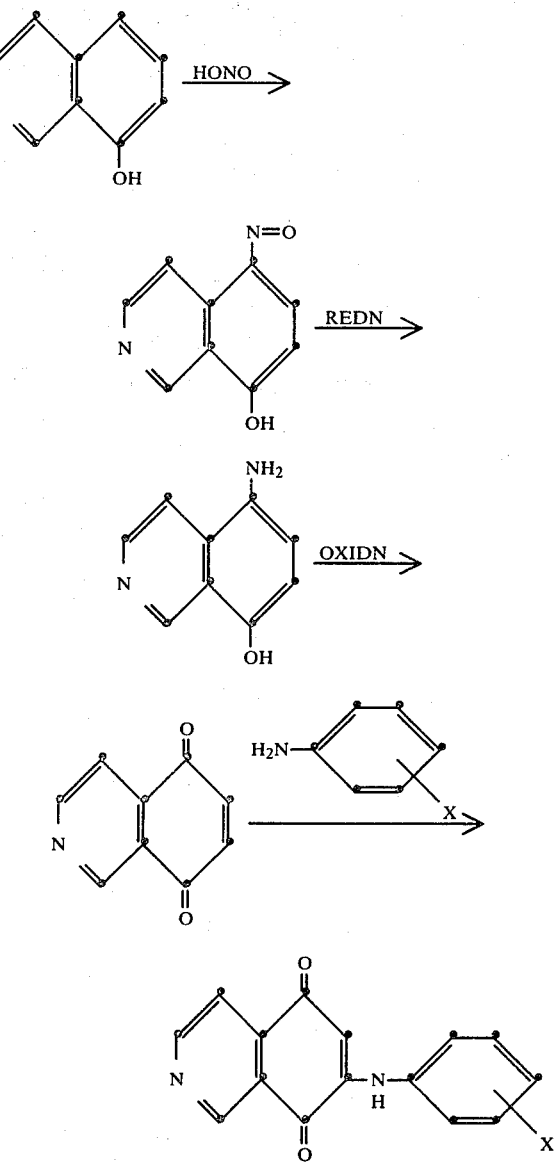

Scheme A

The 8-hydroxyisoquinoline is reacted with nitrous acid to form 5-nitroso-8-hydroxyisoquinoline. The nitrous acid is generated in situ by the action of mineral acid, such as hydrochloric, sulfuric, and the like, on sodium nitrite usually under cold temperature conditions.

The nitroso compound is then reduced by hydrogen gas using a metal catalyst, such as Raney nickel, platinum, or palladium; by an acid and an appropriate metal, such as zinc, iron, or tin; by ammonium sulfide; by lithium aluminum hydride; by phenylhydrazine; and the like, to form the amino-substituted group. The preferred reduction method is catalytic hydrogenation.

The hydroxy and amino groups are then oxidized by aqueous potassium or sodium dichromate; by chromic acid; by ferric chloride; by chromium (III) oxide in glacial acetic acid or pyridine; by permanganate; and the like, to form isoquinoline-5,8-quinone. The preferred oxidizing agent is potassium dichromate.

A solution of the aniline is added to the isoquinone in the presence of an organic solvent. Such solvents as 1,2-dimethyoxyethane, ethanol, and the like may be employed. The reaction is usually allowed to proceed at room temperature, although elevated temperatures, up to the reflux temperature of the solvent, can be used. Additionally, the introduction of catalytic amounts of cerium chloride is desirable in order to facilitate condensation. The reaction is worked up in the usual manner and the desired product may be purified by conventional means, such as crystallization or chromatography.

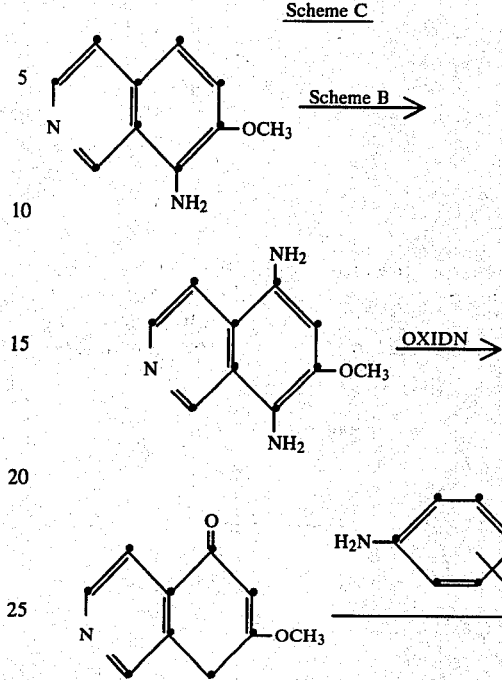

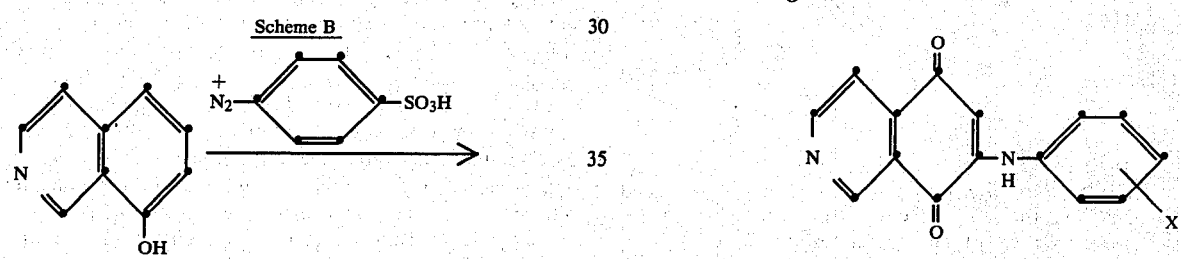

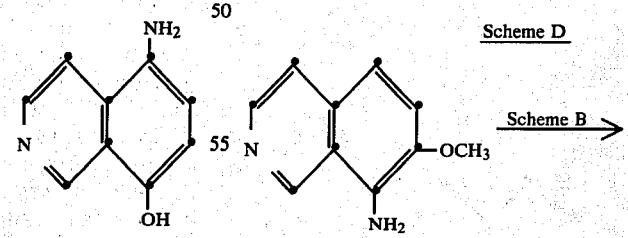

The 8-hydroxyisoquinoline is coupled with a 4-diazobenzenesulfonic acid salt (chloride, fluoborate) in mildly alkaline solution to form the azo compound. The diazonium salt can be formed by dissolving the appropriate aniline in cold aqueous mineral acid and treating with sodium nitrite.

Sodium dithionite (hyposulfite) is then used to form the 5-amino compound from the azo compound in hot, aqueous, mildly alkaline solution.

The 5,8-diamino-7-methoxyisoquinoline is formed from the corresponding 8-amino-7-methoxyisoquinoline by following Scheme B. Then the diamino compound is oxidized to form the diketone, as described in Scheme A; followed by reaction with the amine to form the claimed compounds. In particular, the 7-methoxyisoquinoline-5,8-quinone can be reacted with cerous chloride and the amine to form the 7-substituted amino-isoquinoline-5,8-quinone.

-continued
Scheme D

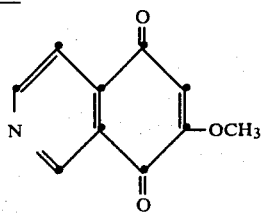

The diamino compound is formed from the corresponding amino compound by following Scheme B. Then the diamino compound is oxidized by Fremy's salt (potassium nitrosodisulfate) to form the isoquinoline-5,8-quinone.

Scheme E

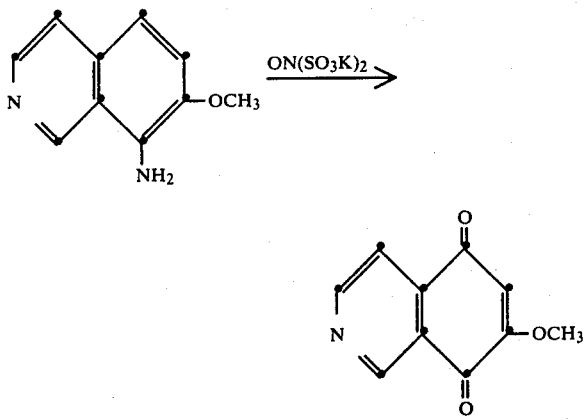

The 8-amino-7-methoxyisoquinoline can be oxidized to the diketone, 7-methoxyisoquinoline-5,8-quinone, using Fremy's salt (potassium nitrosodisulfonate) without going through a diamino intermediate.

Scheme F

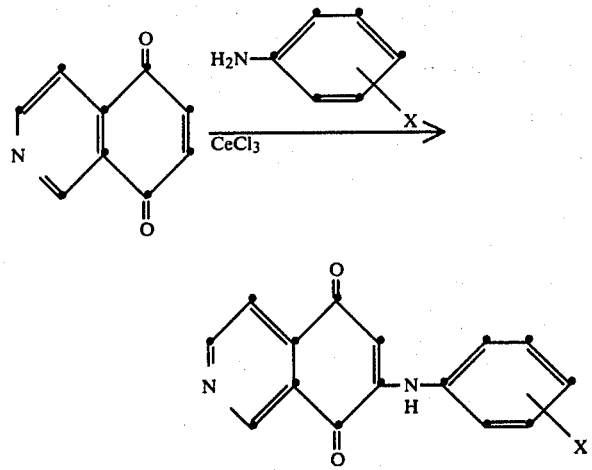

An unsubstituted isoquinoline-5,8-quinone can also be reacted with cerous chloride and a substituted aniline to form 7-substituted anilinoisoquinoline-5,8-quinones, as described in the last step of Scheme C.

In particular, the anilinoisoquinoline-5,8-quinones can be made from the isoquinoline-5,8-quinone and corresponding aniline in a solvent, such as ethanol, and the like. The anilinoisoquinoline-5,8-quinone is then crystallized from the solvent, resulting in the 7-substituted isoquinoline-5,8-quinone.

The preparation of the isoquinoline quinone compounds of this invention is described in the following examples. The examples are illustrative of the compounds embraced by the invention and of the methods commonly employed in their preparation, but are not to be construed as limiting the invention. All temperatures are in degree Celsius.

EXAMPLE 1 isoquinoline-5,8-quinone

Nineteen grams of 5-hydroxy-8-amino-isoquinoline were dissolved in 450 ml of water and 10 ml of concentrated sulfuric acid. The solution was cooled in an ice bath and then 50 ml of a potassium dichromate solution were added. (The dichromate solution was made by dissolving 50 g of potassium dichromate in 500 ml of water.) Forty ml of concentrated sulfuric acid were added, followed by 190 ml of the potassium dichromate solution, then 20 ml of concentrated sulfuric acid, and finally 400 ml of methylene chloride.

The reaction mixture was then stirred slowly and kept at about 25°–30° throughout the reaction. After about 10 minutes, the methylene chloride was separated and 400 ml of fresh methylene chloride were added.

The reaction was continued for another 20 minutes and again the methylene chloride was separated and a further 400 ml of methylene chloride were added. After 40 minutes, the last methylene chloride fraction was separated. All the methylene chloride fractions were then combined and washed with an aqueous sodium chloride solution, then dried with anhydrous sodium sulfate, and evaporated, leaving the product. The product weighed 4 g (21% yield) and the mass spectrum showed the expected molecular ion at m/e=159.

The NMR spectrum (deuterated chloroform) indicated the following:

δ(ppm)=7.1: hydrogen at 6- and 7-position, 7.9: hydrogen at 4-position, 9.2: hydrogen at 3-position, 9.4: hydrogen at 1-position.

The following elemental analysis was obtained:

Calculated for $C_3H_5NO_2$: Theory: C, 67.93; H, 3.17; N, 8.80. Found: C, 67.73; H, 3.25; N, 8.56.

EXAMPLE 2

7-anilinoisoquinoline-5,8-quinone

Three and one-half grams of isoquinoline-5,8-quinone were dissolved in 250 ml of 2 B ethanol and then 6 g of cerious chloride and 2.2 g of aniline were added. The reaction was refluxed for several hours, allowed to cool and stirred overnight at room temperature. After the ethanol was evaporated, the resulting solid formed was dissolved in methylene chloride. The methylene chloride solution was washed twice with aqueous sodium chloride and then once with water. Then the solution was dried with sodium sulfate and the solvent was evaporated. The product was crystallized out of 2 B ethanol, yielding 1.5 g of red crystals.

The mass spectrum indicated the expected molecular ion at m/e=250. The $pk_a$ was 12.3, using 66% aqueous dimethylformamide solution and the apparent molecular weight was 278. In addition, the IR spectrum showed peaks at 1685 and 3360 $cm^{-1}$.

The NMR spectrum (deuterated chloroform) showed the following:

δ(ppm)=6.15: hydrogen at 6-position, 7.4: hydrogens on aniline ring, 7.8: hydrogen at 4-position, 9.15: hydrogen at 3-position, 9.2: hydrogen at 1-position.

The following elemental analysis was obtained:

Calculated for $C_{15}H_{10}N_2O_2$: Theory: C, 71.99; H, 4.03; N, 11.19. Found: C, 71.88; H, 3.90; N, 11.04.

The compounds of formula (I) are useful in treating any clinical condition characterized by excessive release of slow reacting substances of anaphylaxis (leukotrienes; SRS-A), which include immediate-type hypersensitivity reactions such as asthma. Evidence obtained over the past few years has shown the presence of leukotrienes in sputum of patients with chronic bronchitis (Turnbull et al., Lancet II: 526, 1977) or cystic fibrosis (Cromwell et al. Lancet II: 164, 1981), suggesting a role for these substances in the pathology of these diseases. Therefore, the compounds described in this invention also should alleviate some of the symptoms of chronic bronchitis and cystic fibrosis by virtue of their ability to inhibit the release of leukotrienes.

The following test procedure and results demonstrate the utility of the compounds in inhibiting the release of leukotrienes. Male, Hartley guinea pigs, usually 1–2 weeks old were sensitized with respect to ovalbumin by intraperitoneal administration of 0.15 ml hyperimmune serum obtained from guinea pigs actively sensitized against ovalbumin. After 2 days or more, the animals were decapitated, lungs were excised and perfused through the pulmonary artery with Krebs' bicarbonate solution of the following composition in mmoles/liter: KCl, 4.6; $CaCl_2.2H_2O$, 1.8; $KH_2PO_4$, 1.2; $MgSO_4.7H_2O$, 1.2; NaCl, 118.2; $NaHCO_3$, 24.8; and dextrose, 10.0. Poorly perfused and bloody areas were discarded. Normal lung was cut into 1 mm cubes with a McIlwain tissue chopper, washed with Kreb's solution and divided into 400 mg aliquots. The fragmented tissue was then incubated at 37° C. for 15 minutes in Krebs' solution containing indomethacin to optimize SRS-A release and an appropriate concentration of experimental drug. Antigen (ovalbumin) was then added to make a final concentration of $1 \times 10^{-5}$ g/ml. Fifteen minutes later, the incubation medium was decanted and centrifuged at 3,000 g at 4° C. for 5 minutes. The supernatant solution was collected and assayed for SRS-A using a computerized bioassay that employs the isolated guinea pig ileum (Fleisch et al., *J. Pharmacol. Exp. Ther.*, 209, 238–243, 1979, which is incorporated by reference). Release of SRS-A in the presence of an experimental drug was compared to a control sample and the results expressed as percent inhibition of SRS-A release. The compound of Example No. 2 showed a 55 percent inhibition of SRS-A release at $1 \times 10^{-5}$ M concentration.

The compounds or formulations of the present invention may be administered by the oral and rectal routes, topically, parenterally, e.g. by injection, and by continuous or discontinuous intra-arterial infusion. These formulations can be in the form of, for example, tablets, lozenges, sub-lingual tablets, sachets, cachets, elixirs, suspensions, aerosols, and ointments, containing an appropriate amount of the active compound in a suitable base. In addition, they can be soft and hard gelatin capsules, suppositories, injection solutions and suspensions in physiologically acceptable media, or sterile packaged powders adsorbed onto a support material for making injection solutions. Advantageously for this purpose, compositions may be provided in dosage unit form, preferably each dosage unit containing from 5 to 500 mg (from 5.0 to 50 mg in the case of parenteral administration, from 5.0 to 50 mg in the case of inhalation and from 25 to 500 mg in the case of oral or rectal administration) of a compound of formula (I). Dosages of from 0.5 to 300 mg/kg per day, preferably 0.5 to 20 mg/kg of active ingredient may be administered, although it will, of course, readily be understood that the amount of the compound or compounds of formula (I) actually to be administered will be determined by a physician, in the light of all the relevant circumstances, including the condition to be treated, the choice of compound to be administered, and the choice of route of administration. Therefore, the above preferred dosage range is not intended to limit the scope of the present invention.

In this specification, the expression "dosage unit form" is used as meaning a physically discrete unit containing an individual quantity of the active ingredient, generally in admixture with a pharmaceutical diluent therefore, or otherwise in association with a pharmaceutical carrier, the quantity of the active ingredient being such that one or more units are normally required for a single therapeutic administration or that, in the case of severable units such as scored tablets, at least one fraction such as a half or a quarter of a severable unit is required for a single therapeutic administration.

The formulations of the present invention normally will consist of at least one compound of formula (I) mixed with a carrier; or diluted by a carrier or enclosed or encapsulated by an ingestible carrier in the form of a capsule, sachet, cachet, paper or other container; or by a disposable container such as an ampoule. A carrier or diluent may be a solid, semi-solid, or liquid material, which serves as a vehicle, excipient, or medium for the active therapeutic substance.

Some examples of the diluents or carrier which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup U.S.P., methyl cellulose, polyoxyethylene sorbitan monolaurate, ethyl lactate, methyl and propyl hydroxybenzoate, sorbitan trioleate, sorbitan sesquioleate, and oleyl alcohol. Propellants can be trichloromonofluoromethane, dichlorodifluoromethane, dichlorotetrafluoroethane, and the like. In the case of tablets, a lubricant may be incorporated to prevent sticking and binding of the powdered ingredients in the dies and on the punch of the tableting machine. For such purpose there may be employed, for instance, aluminium, magnesium, or calcium stearates; talc; or mineral oil.

Preferred pharmaceutical forms of the present invention are capsules, tablets, suppositories, suspensions, aerosols, injectible solutions, creams, and ointments. The most preferred forms are those used for inhalation application, such as suspensions, aerosols, and the like. Especially preferred is an aerosol formulation for inhalation application.

We claim:

1. A compound of formula (I)

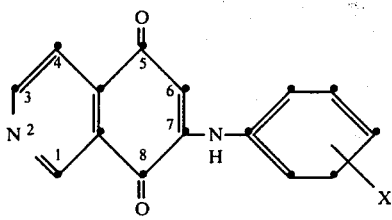

wherein

X is hydrogen, halo, or $C_1$–$C_3$ alkyl.

2. The compound of claim 1 which is 7-anilinoisoquinoline-5,8-quinone.

3. A method of treating an animal, including a human, suffering from or susceptible to any condition characterized by an excessive release of leukotrienes, which comprises administering to said animal a therapeutically-effective amount of a compound of claim 1.

4. The method of claim 3 in which the compound is 7-anilinoisoquinoline-5,8-quinone.

5. A method of treating an animal, including a human, suffering from or susceeptible to an immediate hypersensitivity reaction of the type represented by asthma, which comprises administering to said animal a therapeutically-effective amount of a compound of claim 1.

6. The method of claim 5 in which the compound is 7-anilinoisoquinoline-5,8-quinone.

7. A pharmaceutical formulation useful for conditions characterized by an excessive release of leukotrines which comprises as the active ingredient a therapeutically-effective amount of a compound of claim 1 associated with a pharmaceutically-acceptable carrier therefor.

8. The formulation of claim 7 in which the compound is 7-anilinoisoquinoline-5,8-quinone.

9. The formulation of claim 8 which is formulated for inhalation.

10. The formulation of claim 9 which is formulated as an aerosol.

* * * * *

UNITED STATES PATENT AND TRADEMARK OFFICE
CERTIFICATE OF CORRECTION

PATENT NO. : 4,478,820
DATED : October 23, 1984
INVENTOR(S) : Jerome H. Fleisch, et al.

It is certified that error appears in the above—identified patent and that said Letters Patent is hereby corrected as shown below:

In Claim 1, the right-hand portion of the structural formula at col. 9, lines 5-9, shown as "  " should instead be --- 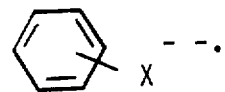 --.

In Claim 5, line 2, "susceeptible" should instead be ---susceptible---.

In Claim 7, line 2, "leukotrines" should instead be ---leukotrienes---.

Signed and Sealed this

Tenth Day of December 1985

[SEAL]

Attest:

DONALD J. QUIGG

Attesting Officer

Commissioner of Patents and Trademarks